(12) United States Patent
Ogawa

(10) Patent No.: US 9,636,009 B2
(45) Date of Patent: May 2, 2017

(54) ENDOSCOPE

(71) Applicant: OLYMPUS CORPORATION, Tokyo (JP)

(72) Inventor: Tomoaki Ogawa, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 134 days.

(21) Appl. No.: 14/673,964

(22) Filed: Mar. 31, 2015

(65) Prior Publication Data

US 2015/0265142 A1    Sep. 24, 2015

Related U.S. Application Data

(63) Continuation of application No. PCT/JP2014/063223, filed on May 19, 2014.

(30) Foreign Application Priority Data

Jun. 25, 2013   (JP) .................................. 2013-132944

(51) Int. Cl.
| | | |
|---|---|---|
| A61B 1/04 | (2006.01) | |
| A61B 1/00 | (2006.01) | |
| A61B 1/267 | (2006.01) | |
| G02B 23/24 | (2006.01) | |
| A61B 1/06 | (2006.01) | |

(52) U.S. Cl.
CPC .......... *A61B 1/2676* (2013.01); *A61B 1/0008* (2013.01); *A61B 1/00071* (2013.01); *A61B 1/00165* (2013.01); *A61B 1/04* (2013.01); *A61B 1/06* (2013.01); *G02B 23/24* (2013.01); *A61B 1/0011* (2013.01)

(58) Field of Classification Search
CPC ........... A61B 1/2676; A61B 1/04; A61B 1/06; A61B 1/00071; A61B 1/00089; A61B 1/00101

USPC ................................................. 600/127, 129
See application file for complete search history.

(56) References Cited

U.S. PATENT DOCUMENTS

| | | | | |
|---|---|---|---|---|
| 4,788,967 A | * | 12/1988 | Ueda .................... | A61B 1/0008 385/119 |
| 2004/0082883 A1 | | 4/2004 | Kohno | |
| 2006/0030753 A1 | * | 2/2006 | Boutillette ......... | A61B 1/00071 600/146 |

FOREIGN PATENT DOCUMENTS

| | | |
|---|---|---|
| CN | 1988842 A | 6/2007 |
| JP | 10-028669 A | 2/1998 |
| JP | 2000-300567 A | 10/2000 |

(Continued)

OTHER PUBLICATIONS

International Search Report dated Aug. 12, 2014 issued in PCT/JP2014/063223.

*Primary Examiner* — Timothy J Neal
(74) *Attorney, Agent, or Firm* — Scully, Scott, Murphy & Presser, P.C.

(57) ABSTRACT

A holding frame made of a material to bear a greater shear stress than a distal end portion rigid portion (a distal end portion) is adhered and fixed to the distal end rigid portion in a state where one end face is exposed from an inclined surface, and an image guide and a light guide are held through the holding frame. In addition, a groove is provided on a side surface of the holding frame and one end of the groove is exposed on a distal end face (the inclined surface) of the distal end rigid portion, to thereby realize downsizing of the distal end portion without lowering durability and improve repairability.

12 Claims, 8 Drawing Sheets

(56) References Cited

FOREIGN PATENT DOCUMENTS

| | | |
|---|---|---|
| JP | 2001-112758 A | 4/2001 |
| JP | 2009-028109 A | 2/2009 |

\* cited by examiner

ENDOSCOPE

CROSS REFERENCE TO RELATED APPLICATION

This application is a continuation application of PCT/JP2014/063223 filed on May 19, 2014 and claims benefit of Japanese Application No. 2013-132944 filed in Japan on Jun. 25, 2013, the entire contents of which are incorporated herein by this reference.

BACKGROUND OF THE INVENTION

1. Field of the Invention

The present invention relates to an endoscope having a distal end portion in which distal end sides of a light guide and an image guide are held.

2. Description of the Related Art

In conventional endoscopes, there is known one which forms an optical image inside a body on a solid-state image pickup device such as a CCD, and displays the image on a monitor, etc. Further, in this type of endoscope, in order to reduce a diameter of a distal end portion of an insertion portion, there is known an endoscope in which the solid-state image pickup device is arranged in an operation portion and an optical image formed by an objective optical system arranged in the distal end portion is conducted to the operation portion through an image guide, and the optical image formed at an emission end of the image guide is produced on the solid-state image pickup device in the operation portion through a relay lens system.

Here, it is general that this type of endoscope has a light guide for transmitting illumination light to the distal end portion in addition to the image guide, and distal end sides of the image guide and the light guide are held by being individually inserted into through holes provided to be close to each other at a distal end rigid portion (see for example Japanese Patent Laid-Open Publication No. 2009-28109).

Incidentally, in an ultrasound endoscope provided with an ultrasound observation section at a distal end portion in addition to an optical observation portion as described above, it is general that a distal end rigid portion made of resin is adopted for the purpose of securing high insulation property.

SUMMARY OF THE INVENTION

An endoscope according to an aspect of the present invention includes: a distal end portion to be inserted into a subject; a guide member that transmits one of light and video information; a holding frame made of a material to bear a greater shear stress than the distal end portion, and holds a distal end side of the guide member by being adhered and fixed in the distal end portion in a state where one end face of the holding frame is exposed from a distal end face of the distal end portion; and at least one groove that is provided on a side surface of the holding frame in an insertion direction of the guide member, and has one end exposed on the distal end face.

DETAILED DESCRIPTION OF THE PREFERRED EMBODIMENTS

Figure 2:
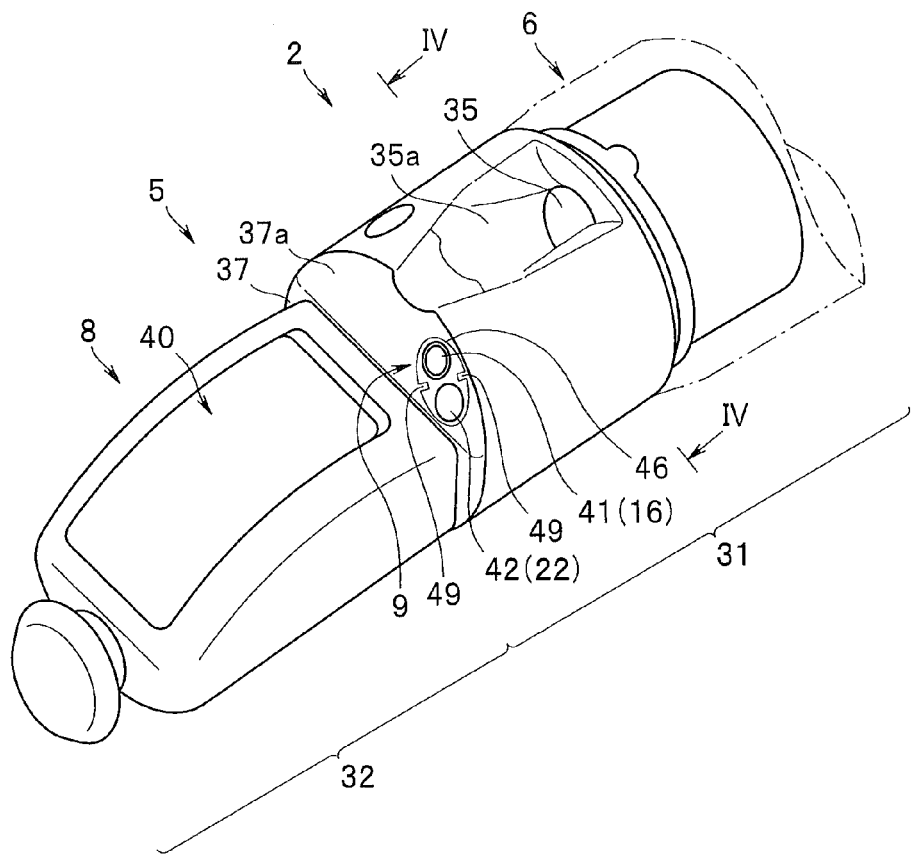
FIG. 2 is a perspective view of a distal end portion as viewed from oblique above.
Figure 3:
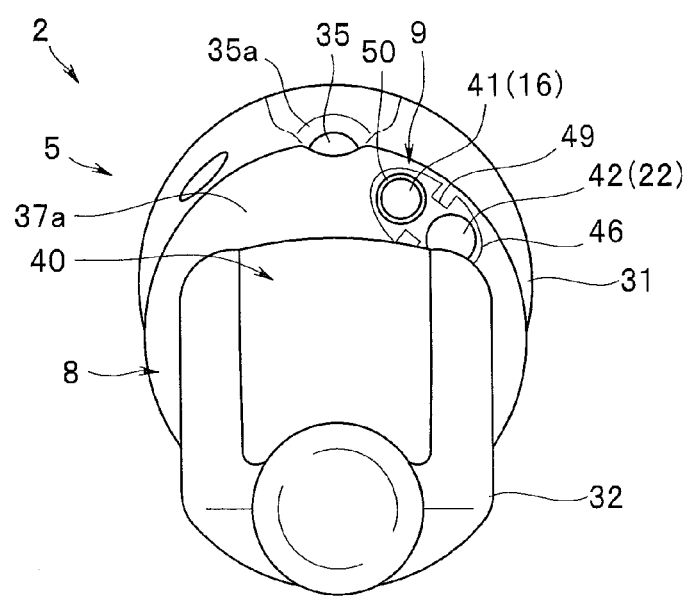
FIG. 3 is a front view of the distal end potion.
Figure 4:
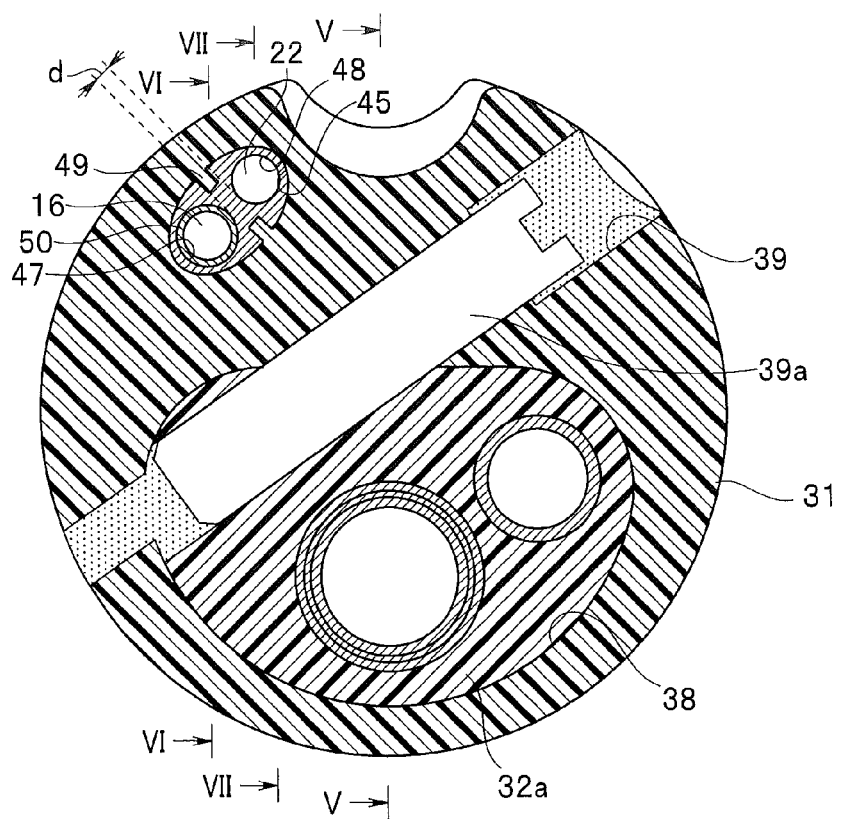
FIG. 4 is a cross sectional view along IV-IV in FIG. 2.
Figure 5:
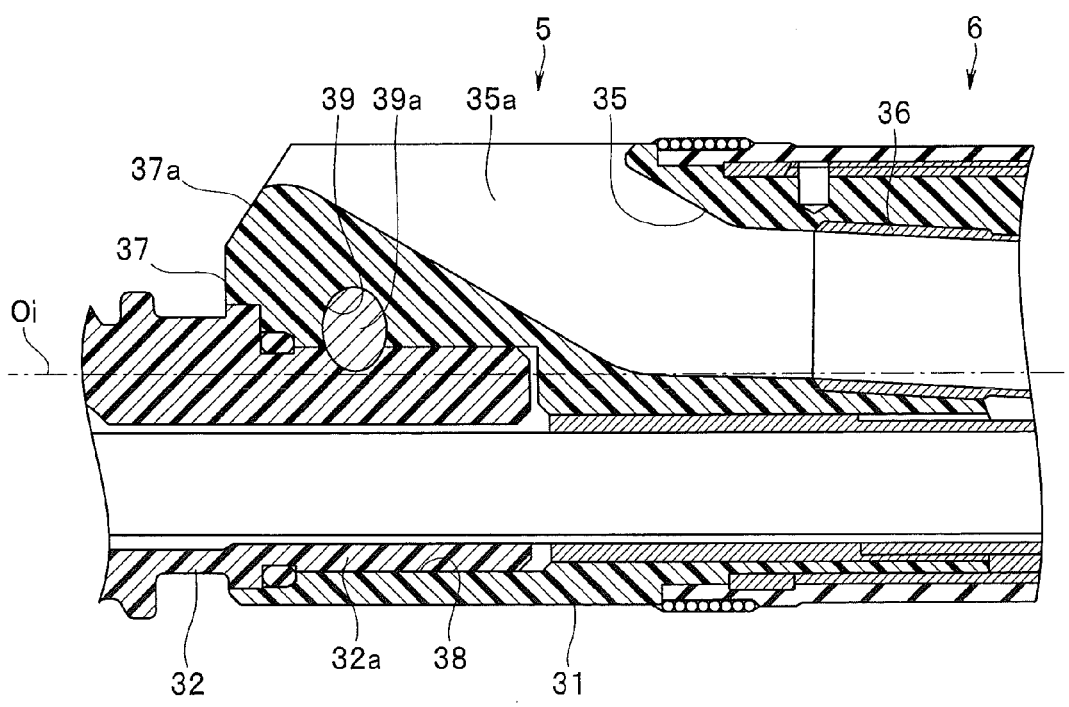
FIG. 5 is a cross sectional view along V-V in FIG. 4.
Figure 6:
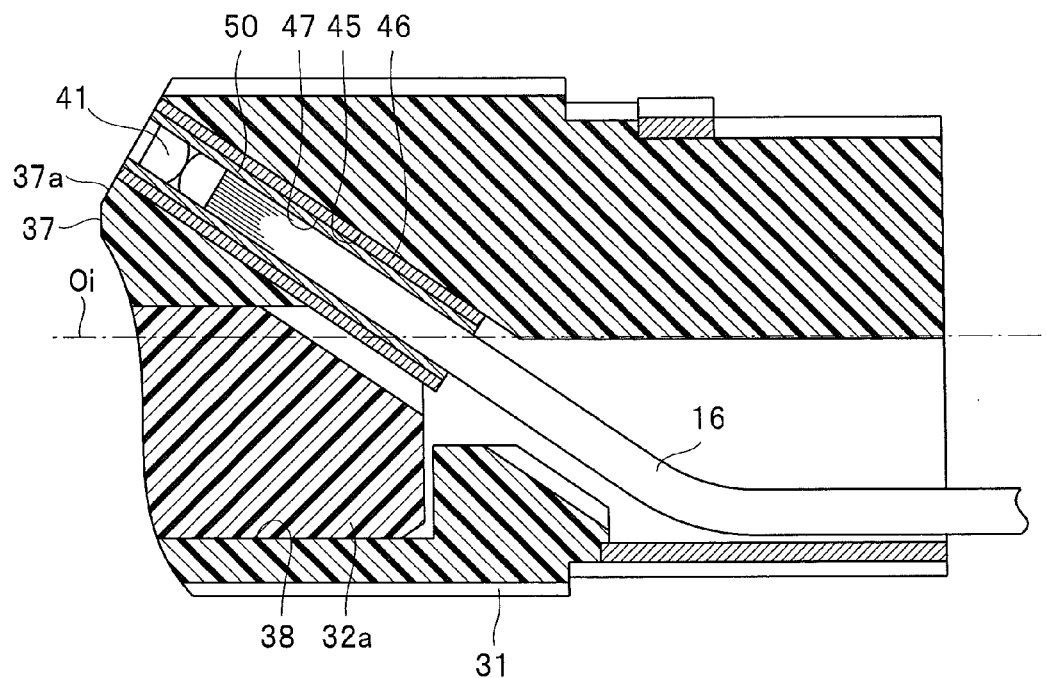
FIG. 6 is a cross sectional view along VI-VI in FIG. 4.
Figure 7:
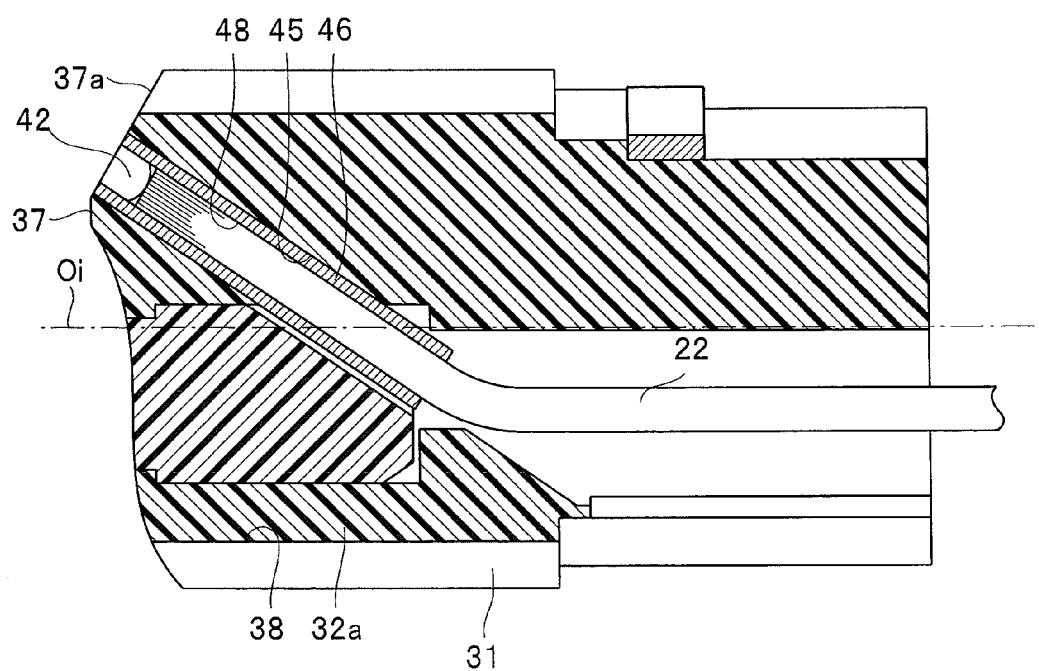
FIG. 7 is a cross sectional view along VII-VII in FIG. 4.
Figure 8:
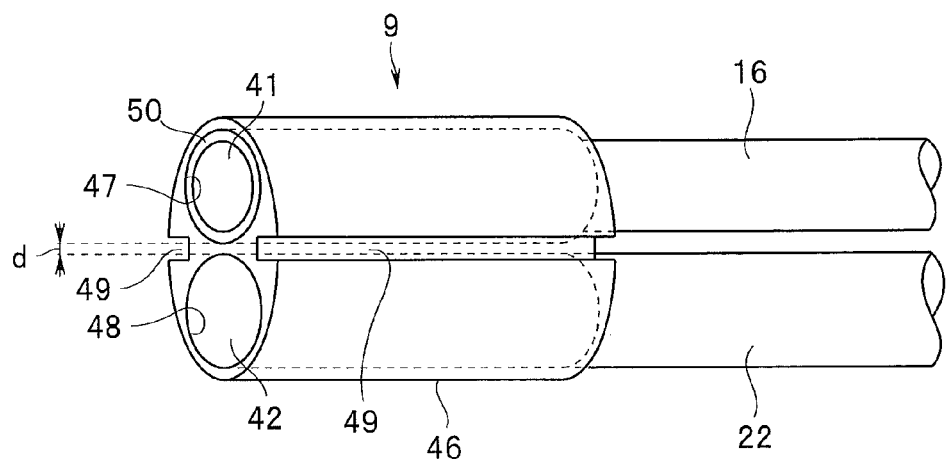
FIG. 8 is a perspective view of a holding frame that holds a light guide and an image guide.
Figure 9:
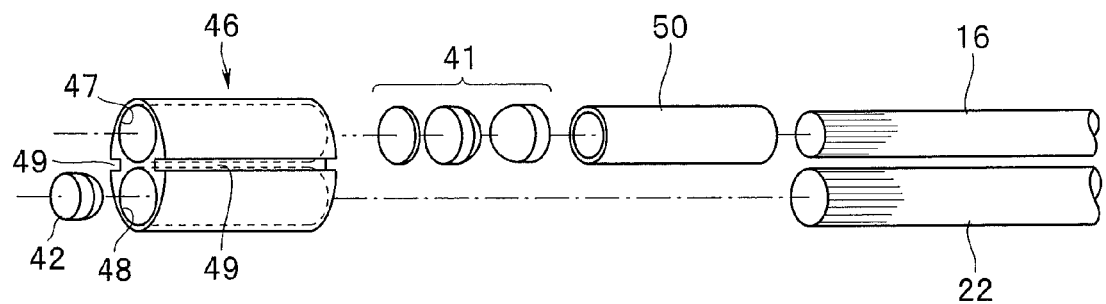
FIG. 9 is an exploded perspective view of the holding frame that holds the light guide and the image guide.
Figure 10:
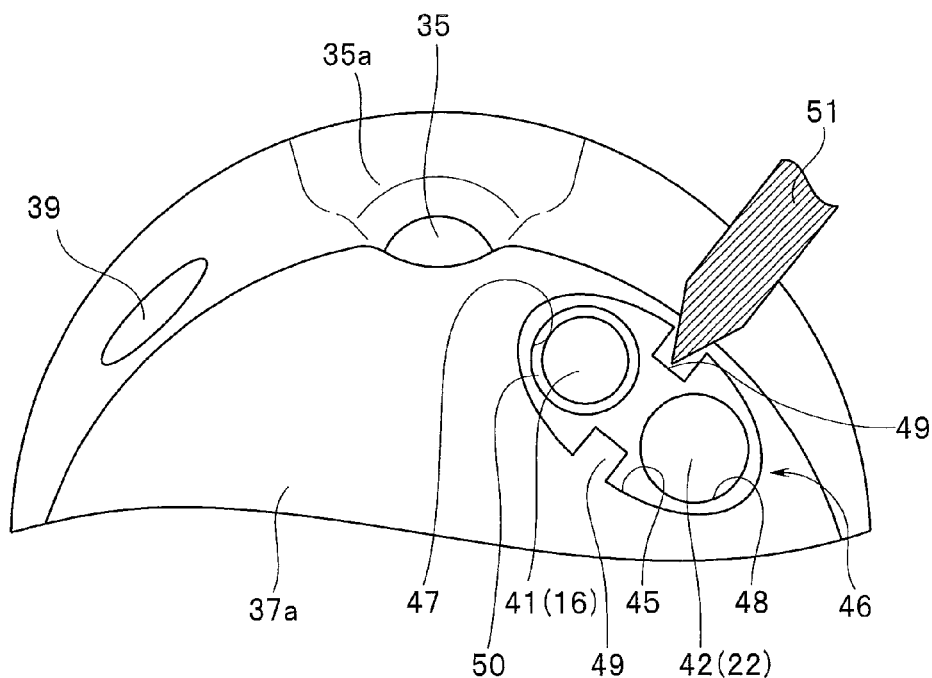
FIG. 10 is an explanatory view when the light guide and the image guide are removed from a distal end rigid portion.
Figure 11:
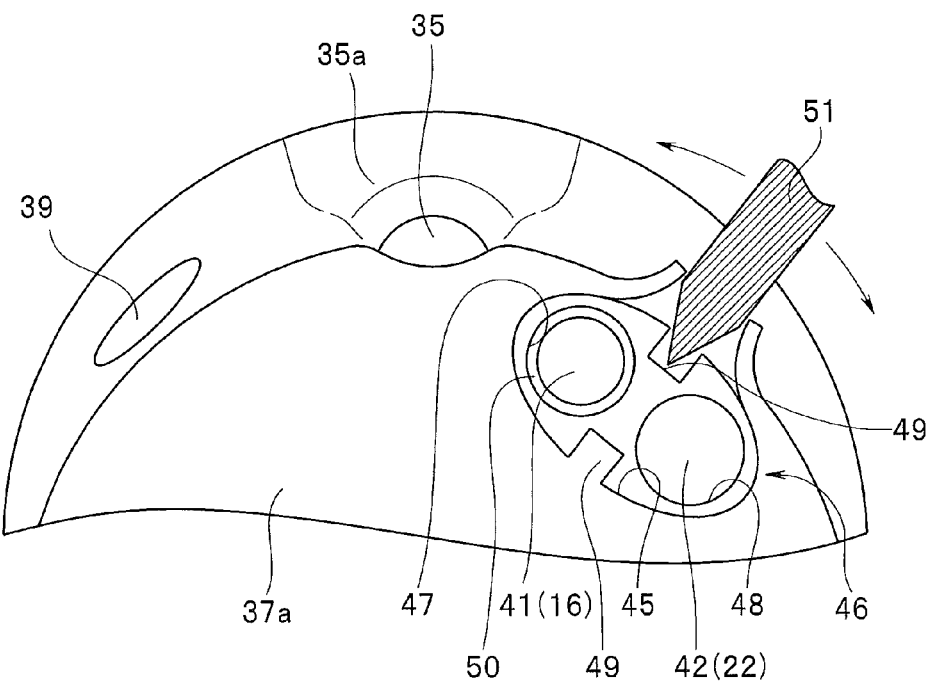
FIG. 11 is an explanatory view when the light guide and the image guide are removed from the distal end rigid portion.

Hereinafter, aspects of the present invention will be described referring to the drawings. The drawings relate to an embodiment of the present invention, and FIG. 1 is an entire view of an endoscope, FIG. 2 is a perspective view of a distal end portion as viewed from oblique above, FIG. 3 is a front view of the distal end potion, FIG. 4 is a cross sectional view along IV-IV in FIG. 2, FIG. 5 is a cross sectional view along V-V in FIG. 4, FIG. 6 is a cross sectional view along VI-VI in FIG. 4, FIG. 7 is a cross sectional view along VII-VII in FIG. 4, FIG. 8 is a perspective view of a holding frame that holds a light guide and an image guide, FIG. 9 is an exploded perspective view of the light guide, the image guide and the holding frame, and FIGS. 10 and 11 are explanatory views when the light guide and the image guide are removed from a distal end rigid portion.

Figure 1:
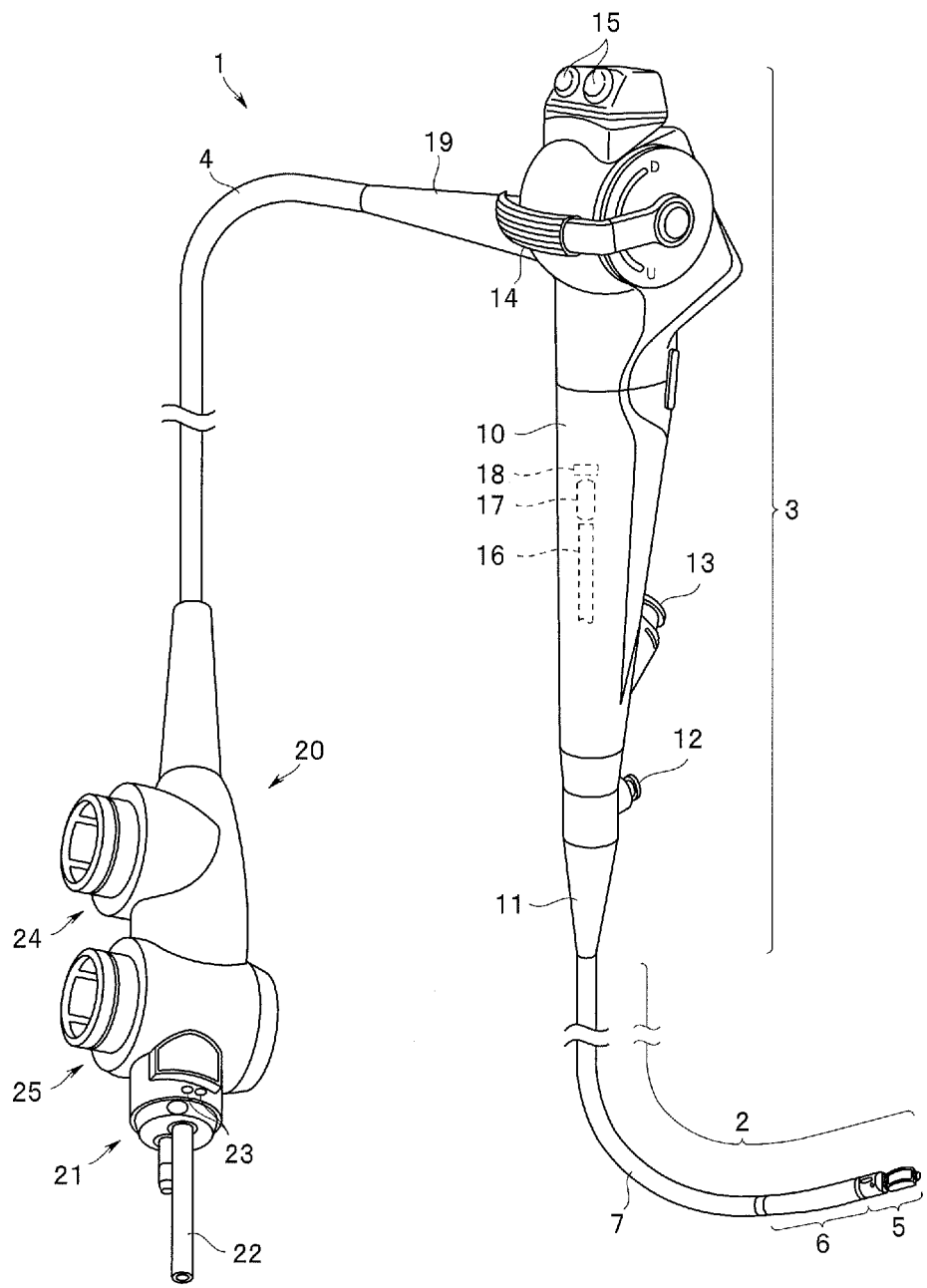
FIG. 1 is an entire view of an endoscope.

An endoscope shown in FIG. 1 is an endoscope for bronchia (a bronchoscope). An enlarged view of a distal end portion 5 in FIG. 1 is shown in FIG. 2, and in the present embodiment, more specifically, the endoscope is an ultrasound bronchoscope which is provided with an ultrasound observation portion 8 for obtaining an ultrasound image and an optical observation section 9 for obtaining an optical image. The endoscope 1 is configured to include an insertion portion 2 which is elongated and capable of being inserted into an observation target region such as bronchia in a subject, an operation portion 3 provided continuously to a proximal end side of the insertion portion 2, and an universal cord 4 extended from a side portion of the operation portion 3.

The insertion portion 2 is configured with the distal end portion 5, a bending portion 6 and a flexible portion 7 that are connected sequentially from a distal end, the bending portion 6 being bendable and disposed on a proximal end side of the distal end portion 5, the flexible portion 7 being elongated, having flexibility and disposed on a proximal end side of the bending portion 6.

The operation portion 3 includes an operation portion body 10 forming an operation grasping portion, and a distal end side of the operation portion body 10 is connected to a proximal end side of the flexible portion 7 through a bending proof portion 11. Further, at locations close to a distal end of the operation portion body 10, an air/water feeding port 12, as an opening portion of an air/water feeding channel (not shown) which is a conduit inside the insertion portion 2, is provided, and a treatment instrument insertion port 13, as an opening portion on a proximal end side of a treatment instrument insertion channel (not shown) which is a conduit for insertion of a treatment instrument into the insertion portion 2, is provided. On the other hand, at locations close to a proximal end of the operation portion body 10, an angle lever 14 for bending operation of the bending portion 6 is provided, and switches 15 for various endoscope functions are provided. Further, inside the operation portion 3, a proximal end side of an image guide 16 is placed, and further a solid-state image pickup device 18 such as a CCD for forming an optical image transmitted from the image guide through a relay lens system 17 is provided.

One end side of the universal cord 4 is provided continuously to a side portion of the operation portion body 10 through a bending proof portion 19. On the other hand, at an extended end which is the other end side of the universal cord 4, a scope connector portion 20 is provided. At an end portion of the scope connector portion 20, there is provided a light source side connector 21 which is attachable to and detachable from a light source apparatus not shown. At the light source side connector 21, a proximal end portion of a light guide 22 that extends from a side of the insertion portion 2 is provided to protrude, and electric contact points 23 are disposed, and when the light source side connector 21 is connected to the light source apparatus, the light guide 22 is optically connected to a light source in the light source apparatus and the electric contact points 23 are electrically connected to a power supply in the light source apparatus. Further, at a side portion of the scope connector portion 20, there are provided an ultrasound connector 24 which is attachable to and detachable from a ultrasound observation apparatus not shown, and an electric connector 25 which is attachable to and detachable from a video processor not shown.

Next, a configuration of the distal end portion 5 in the above endoscope 1 will be described referring to FIGS. 2-9. As shown in FIGS. 2 and 3, the distal end portion 5 includes a distal end rigid portion 31 having a proximal end side continuously connected to the bending portion 6.

The distal end rigid portion 31 is formed of hard resin or the like, for example. A channel communication hole 35 is provided by boring inside the distal end rigid portion 31, and at a proximal end side of the channel communication hole 35, a connecting fitting 36 for connection with a distal end side of the treatment instrument insertion channel is fitted (see FIG. 5). On the other hand, a distal end side of the channel communication hole 35 is opened on a circumferential surface of the distal end rigid portion 31, and this opening portion is set as a suction/forceps port 35a.

Further, on a distal end face 37 of the distal end rigid portion 31, a housing retaining hole 38 for retaining a housing 32 of the ultrasound observation portion 8 is provided (see FIGS. 4 and 5). The housing retaining hole 38 is formed by a hole portion that extends, for example, in an insertion axis Oi direction of the insertion portion 2. Furthermore, on the circumferential surface of the distal end rigid portion 31, a pin hole 39 is provided by boring, and the pin hole 39 communicates with the housing retaining hole 38 in the distal end rigid portion 31.

A pipe portion 32a protruding from a proximal end side of the housing 32 is inserted into the housing retaining hole 38, and the pipe portion 32a is engaged with a fixing pin 39a which is inserted into the pin hole 39 and thereby the housing 32 is retained with respect to the distal end rigid portion 31. Further, an ultrasound transducer 40 of a convex type, for example, is housed in the housing 32, and thereby the ultrasound observation portion 8 is configured at the distal end portion 5.

Further, at a region of the distal end face 37 of the distal end rigid portion 31, which is in the vicinity of the suction/forceps port and is offset to one side with respect to the insertion axis Oi, there is formed an inclined surface 37a which is inclined at a predetermined angle with respect to the insertion axis Oi.

On the inclined surface 37a of the distal end face 37, an objective lens 41 and an illumination lens 42 constituting an optical observation portion 9 are disposed. In this embodiment, the objective lens 41 and the illumination lens 42 are held in the distal end rigid portion 31 with the image guide 16 and the light guide 22, through a holding frame 46.

Specifically, as shown in FIGS. 6 and 7, for example, a holding hole 45 with a distal end side that opens on the inclined surface 37a is provided in the distal end rigid portion 31, and the holding frame 46 is fixed in the holding hole 45.

The holding frame 46 is formed by a member that is made of metal in a shape of an approximately elliptic cylinder, and bears a greater shear stress than the distal end rigid portion 31, as shown in FIGS. 4 and 8, for example. Inside the holding frame 46, a first through hole 47 and a second through hole 48 that extend in the insertion axis Oi direction (more specifically, in a direction inclined by a predetermined angle with respect to the insertion axis Oi) are provided by boring, and further on a side surface (an outer circumferential surface) of the holding frame 46, a pair of grooves 49 extending along axial directions of the through holes 47 and 48 are provided by cutting.

Here, it is desirable that an inter-hole distance d of the first and second through holes 46 and 47 (see FIGS. 4 and 8) is set to be as small as possible, and the distance is set to be 0.1 mm, for example. Further, it is desirable that the grooves 49 are provided at a portion having a large thickness on the holding frame 46, and the grooves 49 in the present embodiment are arranged at portions having the largest thickness, between the first and the second through holes 47 and 48.

As shown in FIGS. 6-9, a mouthpiece 50 which holds objective lenses 41 and a distal end side of the image guide 16 to be united is inserted into the first through hole 47, and is fixed to the first through hole 47 with an adhesive or the like. Further, the illumination lens 42 and a distal end side of the light guide 22 are inserted into the second through hole, and are fixed to the second through hole 47 with an adhesive of the like.

Further, the holding frame 46, which holds the image guide 16 and the light guide 22 with the objective lenses 41 and the illumination lens 42 integrally, is inserted into the holding hole 45 and fixed to the hole with an adhesive of the like. At that time, the holding frame 46 is fixed in a state of being positioned such that one end face of the holding frame is flush with the inclined surface 37a (see FIGS. 6 and 7), and one of the pair of grooves 49 is close to a peripheral portion of the distal end face 37 (the inclined surface 37a) (see FIGS. 3 and 4). Thereby, respective one ends of the grooves 49 are exposed on the inclined surface 37a, and one of the grooves 49 is arranged in the vicinity of the circumferential surface of the distal end rigid portion 31.

According to the above embodiment, the holding frame 46 made of material that bears the greater shear stress than that of the distal end rigid portion 31 (the distal end portion 5) is adhered and fixed to the distal end rigid portion 31 in a state where the one end face is exposed from the inclined surface 37a, and the image guide 16 and light guide 22 are held through the holding frame 46, and thereby downsizing of the distal end portion 5 can be realized without lowering durability. That is, the first and second through holes 47 and 48 for holding the image guide 16 and the light guide 22 are provided in the holding frame 46 which is formed by the material that bears the greater shear stress than that of the distal end rigid portion 31, and thereby the inter-hole distance d can be set to be small while maintaining durability in comparison with a case where these through holes 47 and 48 are provided in the distal end rigid portion 31, and consequently it is possible to facilitate downsizing of the distal end rigid portion 31 (the distal end portion 5).

In addition, the grooves 49 are provided on the side surface of the holding frame 46 that bears the greater shear stress than the distal end rigid portion 31, and the one ends of the grooves 49 are exposed on the distal end face 37 (the inclined surface 37a) of the distal end rigid portion 31, and thereby in making repairs, for example, in a case where a part other than the optical observation section 9 is failed, the image guide 16 and the light guide 22 can be easily removed from the distal end rigid portion 31 and reused without breaking these components, so that repairability can be improved. That is, as shown in FIGS. 10 and 11, for example, a blade 51 of a cutter or the like is brought into contact with the distal end rigid portion 31 using one end of the groove 49 exposed from the inclined surface 37a as a mark, and the distal end rigid portion 31 is incised along the groove 49, and thereby the optical observation section 9 which is reusable can be easily removed from the distal end rigid portion 31.

Figure 12:
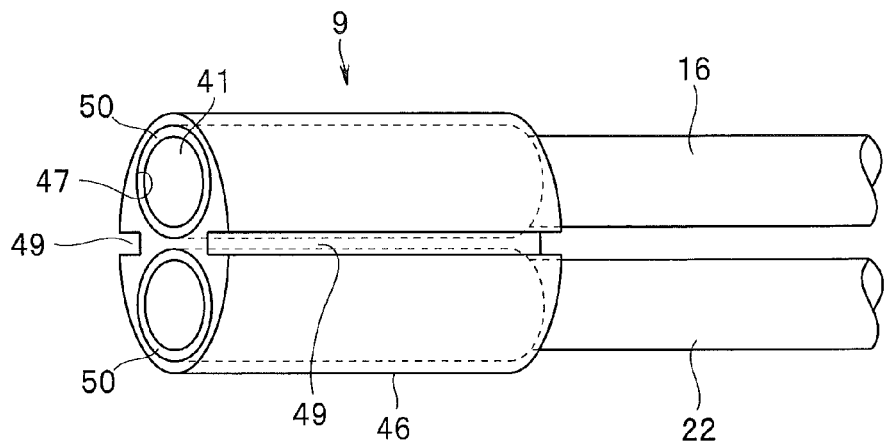
FIG. 12 is a perspective view showing a modified example of the holding frame that holds the light guide and the image guide.

Here, in the above embodiment, one example of the configuration in which only the objective lenses 41 and the image guide 16 are held in the holding frame 46 through the mouthpiece 50 is described, but for example, as shown in FIG. 12, it is possible that the illumination lens 42 and the light guide 22 are adhered and fixed to the holding frame 46 through the mouthpiece 50. Alternatively, although not shown, is it possible that the objective lenses 41 and the image guide 16 are directly adhered and fixed to the first through hole 47 of the holding frame 46 without the mouthpiece intervened.

Figure 13:
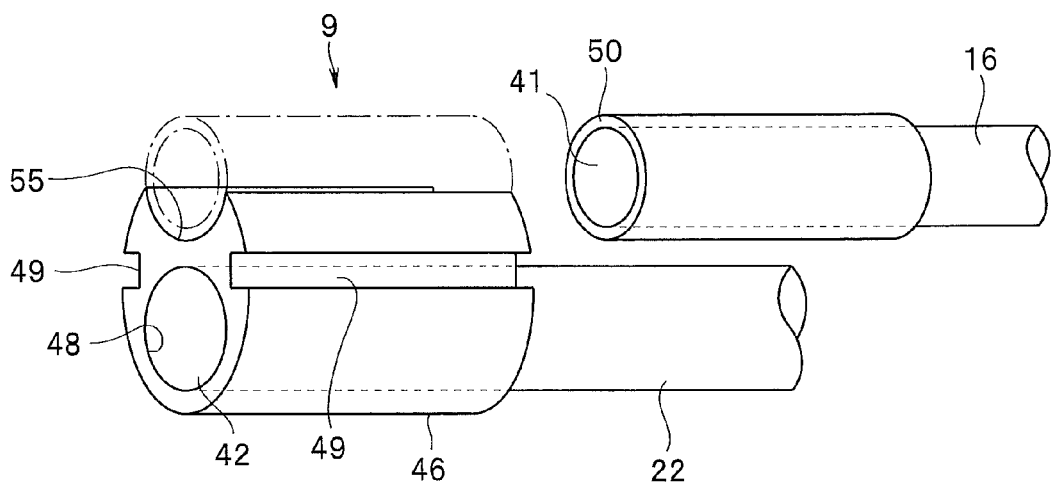
FIG. 13 is a perspective view showing a modified example of the holding frame.

Further, various modifications are possible with respect to the configuration of the holding frame 46. For example, as shown in FIG. 13, instead of one of the first and second through holes (the first through hole in the example shown in FIG. 13), a fitting groove (a first fitting groove 55) is provided on the holding frame 46, and one of the image guide 16 and the light guide 22 with associated elements (e.g. the image guide 16 with associated elements) can be held in the fitting groove 55. With this configuration, a holding structure of the image guide and the light guide 22 with associated elements can be more reduced in size. In this case also, the grooves 49 can be provided on the holding frame 46 without increasing size of the holding frame 46 by arranging the grooves 49 between the fitting groove and the through hole (e.g. between the first fitting groove 55 and the second through hole 48).

Figure 14:
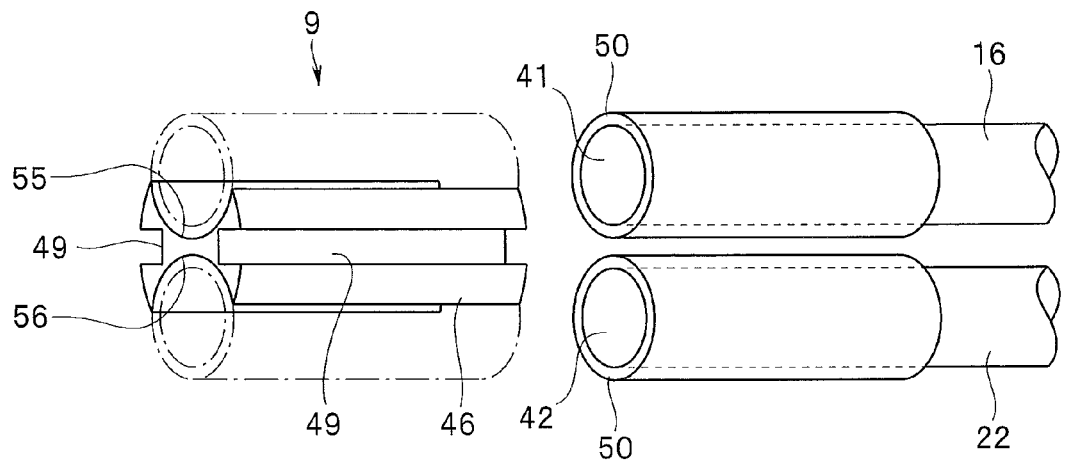
FIG. 14 is a perspective view showing a modified example of the holding frame.

Alternatively, for example, as shown in FIG. 14, it is possible that first and second fitting grooves 55 and 56 are provided on the holding frame, instead of the first and second through holes, and the image guide 16 and the light guide 22 are fixed to the fitting grooves 55 and 56, respectively, through the mouthpieces 50. With this configuration, a holding structure of the image guide and the light guide 22 can be further reduced in size. In this case also, the grooves 49 can be provided on the holding frame 46 without increasing size of the holding frame 46 by arranging the grooves 49 between the first and second fitting grooves 55 and 56.

Figure 15:
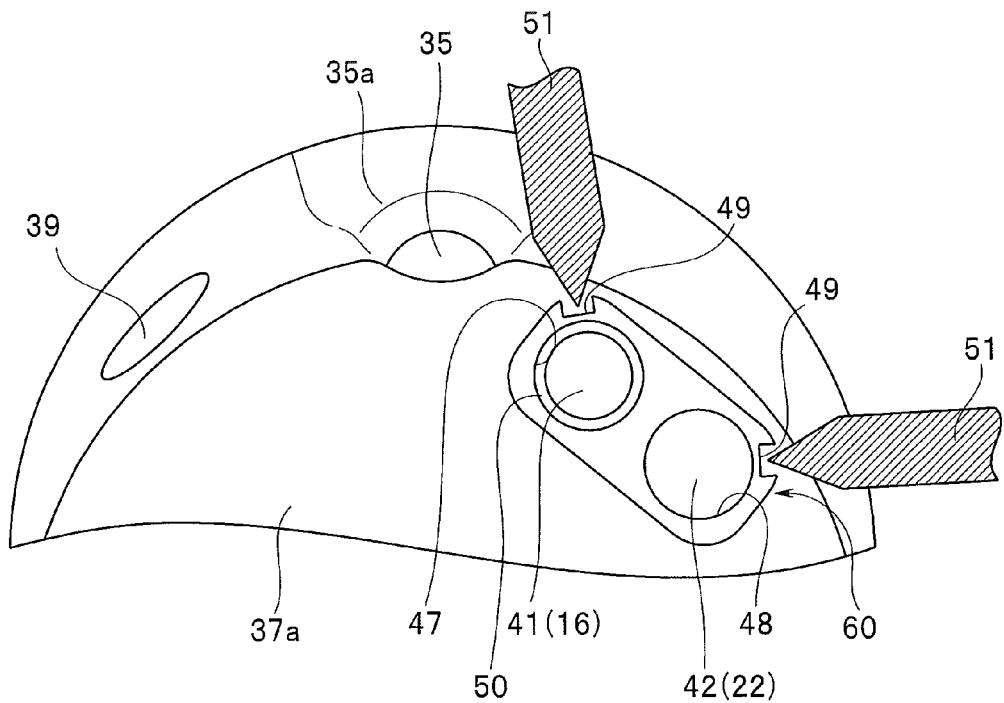
FIG. 15 is an explanatory view when the light guide and the image guide are removed from the distal end rigid portion.
Figure 16:
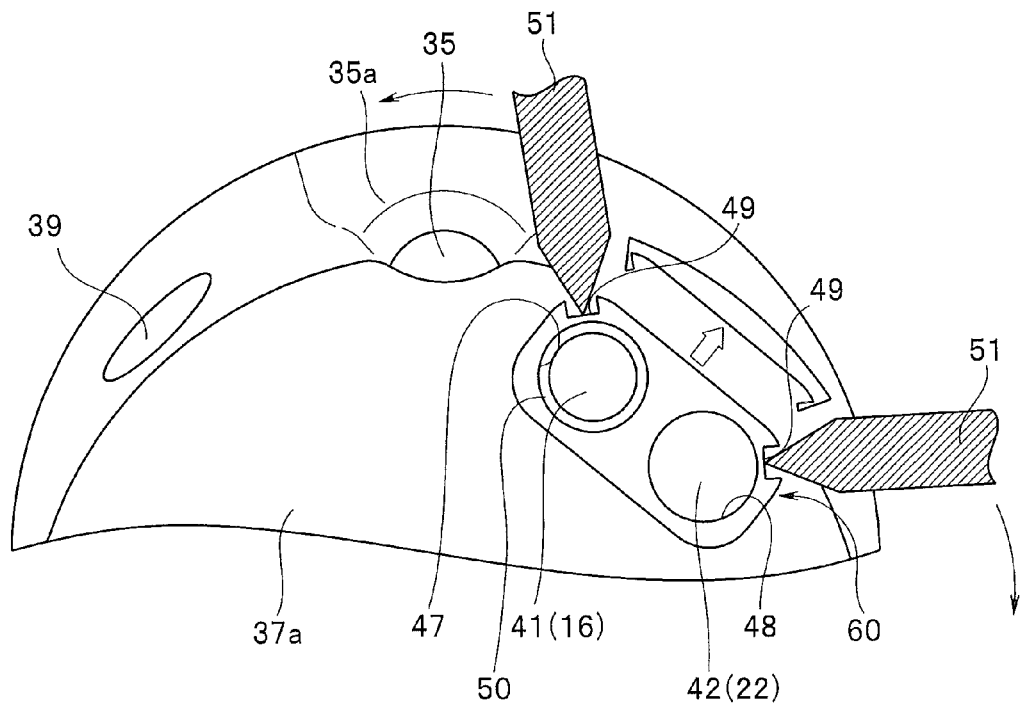
FIG. 16 is an explanatory view when the light guide and the image guide are removed from the distal end rigid portion.

Further, various modifications are possible with respect to the shape of the holding frame 46. For example, instead of the holding frame 46 in the shape of an approximately elliptic cylinder, a holding frame 60 in a shape of an approximately prism can be adopted, as shown in FIGS. 15 and 16. In this case, a space for forming the groove 49 can be secured appropriately at one of four corners of the holding frame 60, as well at a location between the through holes 47 and 48. Further, in these four corners, at regions close to the peripheral portion of the distal end face 37 (the inclined surface 37a), the grooves 49 can be provided. With this configuration, the blade 51 of the cutter or the like is brought into contact with the distal end rigid portion 31 at two places using each one end of the grooves 49 as a mark, and the distal end rigid portion 31 is incised along the grooves 49, and thereby the optical observation section 9 can be more easily removed from the distal end rigid portion 31. Besides, the example shown in the figures concerns a case where the grooves 49 are provided at two places, but it is a matter of course that the grooves may be provided at two places or more, for example, by further providing a groove between the first and second through holes 47 and 48.

Besides, the present invention is not limited to the foregoing embodiments and various modifications and changes are possible, and those modifications and changes are within a technical scope of the present invention. For example, it is a matter of course that the configurations of the foregoing embodiments or modified examples may be appropriately combined. Further, the present invention can be applied to a rigid endoscope which does not include a bending portion and has a rigid insertion portion.

Further, in the foregoing embodiments, one example in which the present invention is applied to the bronchoscope which requires reduction in diameter is described, but the present invention is not limited to this and is applicable to an endoscope or the like for a digestive organ, a circulatory organ, brain surgery, a urinary organ, a genital organ, for example.

What is claimed is:

1. An endoscope comprising:
  a distal end portion to be inserted into a subject, the distal end portion being made of a first material and including a distal end face;
  one or more guide members that transmit one of light and video information;
  a holding frame configured to be capable of bearing a greater shear stress than the distal end portion by being made of a second material capable of bearing a greater shear stress than the first material, the holding frame including one end face, the holding frame holding a distal end side of the guide member by being adhered and fixed in the distal end portion in a state where the one end face of the holding frame is exposed from the distal end face of the distal end portion; and
  at least one groove including one end, the at least one groove being provided on a side surface of the holding member in an insertion direction of the guide member, and having the one end exposed on the distal end face, wherein the holding frame is located eccentrically on the distal end face, and the at least one groove comprises two grooves, the two grooves having the same configuration and being provided on the side surface of the holding frame at regions close to a peripheral portion of the distal end face.

2. The endoscope according to claim 1, wherein the second material is a metal.

3. The endoscope according to claim 1, further comprising a mouthpiece provided between the holding frame and the guide member.

4. An endoscope comprising:
a distal end portion to be inserted into a subject. the distal end portion being made of a first material and including a distal end face;
one or more guide members that transmit one of light and video information;
a holding frame configured to be capable of bearing a greater shear stress than the distal end portion by being made of a second material capable of bearing a greater shear stress than the first material, the holding frame including one end face, the holding frame holding a distal end side of the guide member by being adhered and fixed in the distal end portion in a state where the one end face of the holding frame is exposed from the distal end face of the distal end portion; and
at least one groove including one end, the at least one groove being provided on a side surface of the holding member in an insertion direction of the guide member, and having the one end exposed on the distal end face,
wherein the guide member comprises a light guide for transmitting light to the distal end portion, and an image guide for transmitting video information obtained at the distal end portion, and
wherein the holding frame has a first through hole to which the image guide is inserted to be held, and a second through hole to which the light guide is inserted to be held, and the at least one groove is provided between the first through hole and the second through hole.

5. The endoscope according to claim 4, wherein the second material is a metal.

6. The endoscope according to claim 4, further comprising a mouthpiece provided between the holding frame and the guide member.

7. An endoscope comprising:
a distal end portion to be inserted into a subject, the distal end portion being made of a first material and including a distal end face;
one or more guide members that transmit one of light and video information;
a holding frame configured to be capable of bearing a greater shear stress than the distal end portion by being made of a second material capable of bearing a greater shear stress than the first material, the holding frame including one end face, the holding frame holding a distal end side of the guide member by being adhered and fixed in the distal end portion in a state where the one end face of the holding frame is exposed from the distal end face of the distal end portion; and
at least one groove including one end, the at least one groove being provided on a side surface of the holding member in an insertion direction of the guide member, and having the one end exposed on the distal end face,
wherein the guide member comprises a light guide for transmitting light to the distal end portion, and an image guide for transmitting video information obtained at the distal end portion, and
wherein the holding frame has a through hole to which one of the image guide and the light guide is inserted to be held, and a fitting groove to which other of the image guide and the light guide is fitted to be held, and the at least one groove is provided between the through hole and the fitting groove.

8. The endoscope according to claim 7, wherein the second material is a metal.

9. The endoscope according to claim 7, further comprising a mouthpiece provided between the holding frame and the guide member.

10. An endoscope comprising:
a distal end portion to be inserted into a subject, the distal end portion being made of a first material and including a distal end face;
one or more guide members that transmit one of light and video information;
a holding frame configured to be capable of bearing a greater shear stress than the distal end portion by being made of a second material capable of bearing a greater shear stress than the first material, the holding frame including one end face, the holding frame holding a distal end side of the guide member by being adhered and fixed in the distal end portion in a state where the one end face of the holding frame is exposed from the distal end face of the distal end portion; and
at least one groove including one end, the at least one groove being provided on a side surface of the holding member in an insertion direction of the guide, member, and having the one end exposed on the distal end face,
wherein the guide member comprises a light guide for transmitting light to the distal end portion, and an image guide for transmitting video information obtained at the distal end portion, and
wherein the holding frame has a first fitting groove to which the image guide is inserted to be held, and a second fitting groove to which the light guide is inserted to be held, and the at least one groove is provided between the first fitting groove and the second fitting groove.

11. The endoscope according to claim 10, wherein the second material is a metal.

12. The endoscope according to claim 10, further comprising a mouthpiece provided between the holding frame and the guide member.

* * * * *